(12) United States Patent
Kabalka (10) Patent No.: US 7,041,859 B1
(45) Date of Patent: May 9, 2006

(54) METHOD FOR HALOGENATING OR RADIOHALOGENATING A CHEMICAL COMPOUND

(75) Inventor: George W. Kabalka, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 11/174,797

(22) Filed: Jul. 5, 2005

Related U.S. Application Data (60) Provisional application No. 60/608,186, filed on Sep. 9, 2004.

(51) Int. Cl.
C07C 17/20 (2006.01)
C07C 22/00 (2006.01)
C07C 17/00 (2006.01)

(52) U.S. Cl. ............... 570/260; 570/143; 570/144; 570/161; 570/174; 570/175; 570/190; 570/201

(58) Field of Classification Search ............... 570/260, 570/143, 144, 161, 174, 175, 190, 201
See application file for complete search history.

(56) References Cited

U.S. PATENT DOCUMENTS 4,450,149 A    5/1984    Kabalka

OTHER PUBLICATIONS

Kabalka et al (Synthesis of Organic bromide via organotrifluoroborates, Organomettalics 2004, 23, 4519-4521.*

Darses, S, and Genet, J-P, "Cross-coupling reactions of arenediazonium tetrafluoroborates with potassium aryl- or alkenyltrifluoroborates catalyzed by palladium", Tetrahedron Letters, 38(25):4393-4398 (1997).

Darses, S., et al, "Potassium organotrifluoroborates: New Partners in palladium-catalysed cross-coupling reactions", Eur. J. Org. Chem., 1875-1883 (1999).

Kabalka, GW, et al, "Palladium-catalyzed cross-coupling of acetates of Baylis-Hillman adducts and potassium organotrifluoroborates", Organic Letters, 5(21):3803-3805 (2003).

Kabalka GW, and Mereddy AR, "A facile synthesis of aryl iodides via potassium aryltrifluoroborates", Tetrahedron Letters, 45:343-345 (2004).

Kabalka GW, and Mereddy AR, "Iodination of organotrifluoroborates: synthesis of vinyl and alkynyl iodides", Tetrahedron Letters, 45:1417-1419 (2004).

Kabalka GW, and Mereddy AR, "Facile syntheses of organic halides using organotrifluoroborates", Boron Americas IX, San Marcos, TX, (May 19-22, 2004).

Molander GA, and Rivero, MR, "Suzuki Cross-coupling reactions of potassium alkenyltrifluoroborates", Organic Letters 4(1):107-109 (2002).

Molander GA, et al., "Development of the Suzuki-Miyaura cross-coupling reaction: use of air-stable potassium alkynyltrifluoroborates in aryl alkynylations", J. Org. Chem., 67:8416-8423 (2002).

Vedejs, E, et al., "Conversion of arylboronic acids into potassium aryltrifluoroborates: Convenient precursors of arylboron difluoride Lewis acids", J. Org. Chem., 60:3020-3027 (1995).

* cited by examiner

*Primary Examiner*—J. Parsa
(74) *Attorney, Agent, or Firm*—Howard Eisenberg, Esq.

(57) ABSTRACT

A method for obtaining a halogenated organic compound, whereby an organotrifluoroborate compound is reacted with a halide ion in the presence of an oxidizing agent to produce the corresponding halogenated organic compound. The method may be used for producing radiohalogenated organic compounds.

16 Claims, 7 Drawing Sheets

| SUBSTRATE | PRODUCT | SUBSTRATE | PRODUCT |
|---|---|---|---|
|  |  |  |  |
|  |  |  |  |
|  |  |  |  |
|  |  |  |  |

METHOD FOR HALOGENATING OR RADIOHALOGENATING A CHEMICAL COMPOUND

This application claims the benefit of now abandoned U.S. Provisional Application Ser. No. 60/608,186, which was filed on Sep. 9, 2004.

This invention was developed in part by grants from the U.S. Department of Energy and the National Institutes of Health and the U.S. government may have certain rights in the invention.

FIELD OF THE INVENTION

This invention pertains to the field of labeling a chemical compound, and particularly to the field of attaching a halogen label, such as a radioactive halogen, to an organic chemical compound.

BACKGROUND OF THE INVENTION

Radioisotopes, particularly halogen radioisotopes, have been used extensively in nuclear medicine. The preferred utility of radioiodine in nuclear medicine is based on the availability of relatively reliable techniques of incorporating radiohalogen atoms into organic compounds.

Many of the presently available radiohalogenation techniques have the common feature that a radionuclide is introduced into an organic compound by an organometallic reactant, such as organoborane. Traditionally, many radiohalogenated materials have been made by substitution reactions, most of which are nucleophilic. However, some useful electrophilic procedures are known. A major disadvantage of such substitution reactions is that, because the reaction rates are dependent upon the concentration of reagents, the radiohalogenation reactions do not work well on small scales. Consequently, one encounters many difficulties in synthesizing desired radiohalogenated compounds such as the rate of formation, separation of radiolabeled product from the organic starting material and side reactions such as solvent attack on the organic starting material. Yields of only 2–10% are not uncommon in such conventional synthetic procedures. Still another drawback is that the availability of suitable organic starting materials for the radiolabeling reaction is often limited. In many cases the desired substitution reaction does not occur.

An extremely important consequence of the above mentioned reaction rate problem is that no-carrier-added reagents are difficult to prepare. No-carrier-added reagents are very important because the quantity of radiopharmaceutical compound can be kept below picogram levels. This minimizes body loads and aids in the differentiation of receptor-sites.

Kabalka, U.S. Pat. No. 4,450,149, discloses a method for radiohalogenating organoborane compounds. According to Kabalka, the organoborane is reacted with a wide variety of halide salts in the presence of a mild oxidizing agent to provide a radiohalogenated compound. Boron-halogen exchange has been used for preparing a wide variety of radiopharmaceuticals. Initially, methods were developed to halogenate trialkylboranes but it was found that boronic acids and esters were more convenient to handle and could be prepared containing a wide variety of functional groups. However, the use of boronic acids as organohalogen precursors to pharmaceuticals has a disadvantageous propensity to form boroxines that are unstable to both air and water.

One disadvantage of most of the prior art methods of radiolabeling is that they require introduction of a radioisotope early in the construction of the desired molecule due to the fact that the methodologies do not tolerate many pharmacologically active functional groups. This is deleterious because many of isotopes of use in medicine have very short half-lives and will decay before synthesis is complete.

In the light of the above discussed difficulties of preparing radiohalogenated compounds by substitution reactions and despite the advances in radiohalogenation disclosed in Kabalka, a need continues to exist for an improved technique of radiohalogenating organic compounds in high yields and for a method that permits the attachment of a binding site for a radiolabel on an intermediate at any step in the synthesis of a final molecule to be radiolabeled, followed by attachment of the radiolabel at the site following synthesis of the final molecule.

Organotrifluoroborates have proven to be versatile intermediates in organic synthesis because of their remarkable chemical stability. They are crystalline solids that are stable to both air and water, and they are readily prepared. Vedejs et al, J. Organic Chemistry, 60:3020–3027 (1995) discloses a method for the conversion of aryl and alkyl boronic acids into potassium aryl and alkyl trifluoroborates, respectively, by addition of $KHF_2$. Darses et al, European J. Organic Chemistry, 8:1875–1883 (1999) discloses a method for the production of aryl, alkenyl, and alkynyl trifluoroborates.

DESCRIPTION OF THE INVENTION

The present invention is a method for halogenating, including radiohalogenating, an organic chemical compound. The invention provides unexpected advantageous properties compared with presently available methods for such halogenation of a compound. Any organic chemical compound may be halogenated by the method of the invention.

In addition, the method of the invention overcomes the disadvantage of prior art methods of halogenating or radiohalogenating that require one skilled in the art to attach a halogen to an intermediate early in the synthesis of a final molecule. In contrast to such presently available methods of labeling, the method of the invention permits one skilled in the art to attach a halogen or a radiohalogen on an intermediate at any step in the synthesis of a final molecule or on the final molecule itself. The method of the invention further permits the precise introduction of a label at a particular position in a molecule.

In accordance with the method of the invention, an organotrifluoroborate is reacted with a halide ion, which may be a radioactive halide ion, in the presence of an oxidizing agent to produce a corresponding organohalide compound. The reaction of the invention is shown below in Scheme 1. Preferably, the organotrifluoroborate compound and the halide ion are in solution when reacted.

Scheme 1

In Scheme 1:

BF$_3$K=organotrifluoroborate, K may be potassium or other positive cation

R=organic moiety including aryl, heteroaryl, alkenyl, vinyl, alkynyl, alkyl (R may or may not contain functional groups such as ester, acid, hydroxyl, nitrile, nitro, peroxy, aldehyde, lactone, nitroso, halo, imine, and a wide variety of nitrogen, oxygen, and sulfur based heterocycles)

*X$^-$=halide, such as a radioactive halide, including fluoride, iodide, bromide, astatide

[O]=an oxidant, such as air, peracid, peroxide, chloramine-T, halosuccinimide, elemental halogen (X$_2$)

Q=catalytic quantity of an acid or base (optional)

Solvent=solvent in which all constituents of the reaction are dissolved, such as water, acetonitrile, acetone, ethyl ether, and tetrahydrofuran.

The organotrifluoroborate is preferably a potassium organotrifluoroborate. If desired, however, other positive cations may substitute for the illustrated potassium. For example, the positive cation may be one from column 1a of the Periodic Table of the Elements, such as sodium, lithium, potassium, rubidium, cesium, or francium. Other positive cations are also conceived to be suitable, such as ammonium ion, for example as a trialkylammonium ion. Ions other than +1 cations may also be used, for example a +2 cation such as calcium, a +3 cation such as aluminum, or a +4 cation such as tin.

The organic moiety of the organotrifluoroborate may be, for example, an aryl, heteroaryl, alkenyl, vinyl, alkynyl, or alkyl moiety. Other organic moieties are also suitable for the organotrifluoroborate of the method of the invention. The organic moiety may be any organic chemical compound. For example, organic chemical compounds that contain functional groups such as ester, acid, hydroxyl, nitrile, nitro, peroxy, aldehyde, lactone, nitroso, halo, imine, and nitrogen, oxygen, or sulfur based heterocycles are suitable. The organic moiety may be a pharmacologic compound or derivative thereof or intermediate in the production of such pharmacologic compound or derivative, such as an inhibitor of cyclooxygenase such as celecoxib, rofecoxib, or valdecoxib.

The halide that is reacted with the organotrifluoroborate may be radioactive or not radioactive. The halide may be of any of the halogens that belong to the column 7a of the Periodic Chart of the Elements, including fluorine, chlorine, bromine, iodine, and astatine. Examples of radioactive halides that may be reacted with the organotrifluoroborate include fluorine-18, bromine-76, bromine-82, iodine-123, iodine-131, and astatine-211.

The cation portion of the halide that is reacted with the organotrifluoroborate may be any cation that will combine with a halogen to form a halide. For example, the cation may be any one of the group 1a elements of the Periodic Chart of the Elements, including lithium, sodium, potassium, rubidium, cesium, and francium.

The choice of oxidizing agent for the reaction is immaterial. That is, any oxidant may be used so long as the oxidant is capable of oxidizing the halide ions and preferably does not significantly oxidize portions of the organotrifluoroborate molecule other than the halide ions. This is especially important when the organotrifluoroborate molecule contains functional groups such as alcohols and aldehydes that could be destroyed by overzealous oxidation. Oxidants that are suitable for the method of the invention include air, a peracid such as peracetic acid, a peroxide, chloramine-T, halosuccinimide, tert-butylhydroperoxide, and meta-chlorperoxybenzoic acid (m-CPBA). An elemental form of halogen (X$_2$), such as F$_2$ or Br$_2$ may also be used as the oxidant. Chloramine-T is a preferred oxidant.

The reaction of the organotrifluoroborate with a radioactive halide may be performed in the presence of a catalytic quantity of an acid or base, such as 0.1% NaOH. The presence of the acid or base is preferred but optional. If an acid or base is used, generally either an acid or a base is used and is used in small quantities. Generally, the reaction tends to work better with either an acid or base depending on the particular organic moiety that forms a part of the organotrifluoroborate. One skilled in the art will understand that a base or an acid may or may not be included in the reaction mixture and will add or subtract such acid or base in order to optimize the reaction.

The particular choice of solvent in which the organotrifluoroborate is dissolved is immaterial to the invention. A suitable solvent is any one in which all components of the reaction, including the organotrifluoroborate, the radioactive halide, the oxidant, the acid or base if present, and the reaction product are all soluble. Thus, the solvent may be a polar or nonpolar solvent or may be a mixture of polar and nonpolar solvents. Preferred solvents include tetrahydrofuran (THF), ethanol, water, acetonitrile, acetone, and ethyl ether.

The invention is further described in the following non-limiting examples.

EXAMPLE 1

Production of Organotrifluoroborates

The procedure for obtaining organotrifluoroborate salts is shown schematically in Scheme 2.

Scheme 2

R=an organic moiety, such as alkyl, alkenyl, alkynyl, aryl, or heteroaryl

A solution of a starting organic compound, such as phenylacetylene, (1.02 g, 10.0 mmol) in 20 mL of dry THF was cooled to −78° C. under argon. n-Butyllithium (6.25 mL, 1.60 M in hexane, 10 mmol) was added dropwise and the solution was stirred for one hour. Trimethylborate (1.58 g, 15.0 mmol, 1.5 equiv) was then added dropwise at −78° C. and the solution stirred for one hour. The reaction mixture was then allowed to warm to −20° C. and stirred for an additional hour. A saturated aqueous solution of potassium hydrogen difluoride (4.70 g, 60.0 mmol, 6 equivalents) was added to the vigorously stirred solution. The resulting mixture was allowed to stir for one hour at −20° C., after which it was allowed to warm to room temperature. The solvent was removed under reduced pressure and the resulting white solid was dried under high vacuum for two hours to remove all water. The solid was then washed with acetone (20 mL) and then with hot acetone (20 mL). The resulting organic solution was filtered and the solvent removed to afford a white solid. The solid was recrystallized from hot acetonitrile to produce the desired product (1.41 g, 68%).

By this method, alkyl, alkenyl, and alkynyl trifluoroborate salts were obtained from starting materials in which R was one of the following: phenyl (trans), phenyl (cis), 4-methylphenyl, 1-cyclohexenyl, 1-chloropropyl, 4-chlorophenyl, 4-bromophenyl, hexyl, tert-butyl, 4-methoxyphenyl, 4-cyanophenyl, 1-hydroxybutyl, tert-butyldimethylsilyloxybutyl, 4-trifluoromethylphenyl, heptyl, 2,4-dimethylphenyl, 4-acetylphenyl, 3-nitrophenyl, 1-napththalenyl, and 3-thienyl.

EXAMPLE 2

Synthesis of Aryl Iodides

A variety of aryltrifluoroborates, synthesized as described in Example 1, were subjected to radioiodination using no-carrier added Na$^{123}$I and peracetic acid in 50% aqueous THF to yield the corresponding aryliodides. The general formula for this reaction is shown below in Scheme 3. All reactions were carried out using dry solvents under an inert atmosphere.

Scheme 3

$$ArBF_3K \xrightarrow[\text{Chloramine-T}]{NaI} ArI$$

Ar = Aryl or heteroaryl

EXAMPLE 2a

Radiosynthesis of 4-[$^{123}$I]iodoanisole
(Representative Procedure)

Para-methoxyphenyltrifluoroborate (100 µL of 5.2×10$^{-2}$ solution in 50% aqueous tetrahydrofuran) was placed in a 2 mL Wheaton vial containing no-carrier-added Na$^{123}$I (37 MBq in 0.1% aqueous NaOH). To this was added peracetic acid (100 µL, 0.3% solution in methanol). The reaction vial was sealed, covered with aluminum foil, and the mixture stirred for 10 min at room temperature. A drop of 10% aqueous sodium thiosulfite was added to decompose excess iodine and the radioiodinated product was isolated by passing it through a silica gel Sep-Pak cartridge using petroleum ether: ethyl acetate (50:1) as eluent. The radiochemical purity of 4-[$^{123}$I]iodoanisole was determined by radio-TLC (aluminum backed silica gel plate, hexane:ethyl acetate=50:1); R$_f$=0.55. The TLC retention time (and that of all products) was identical to that of authentic samples. The radiochemical purity was 98% and the radiochemical yield was 88%. The total synthesis time was 20 min.

Figure 1:
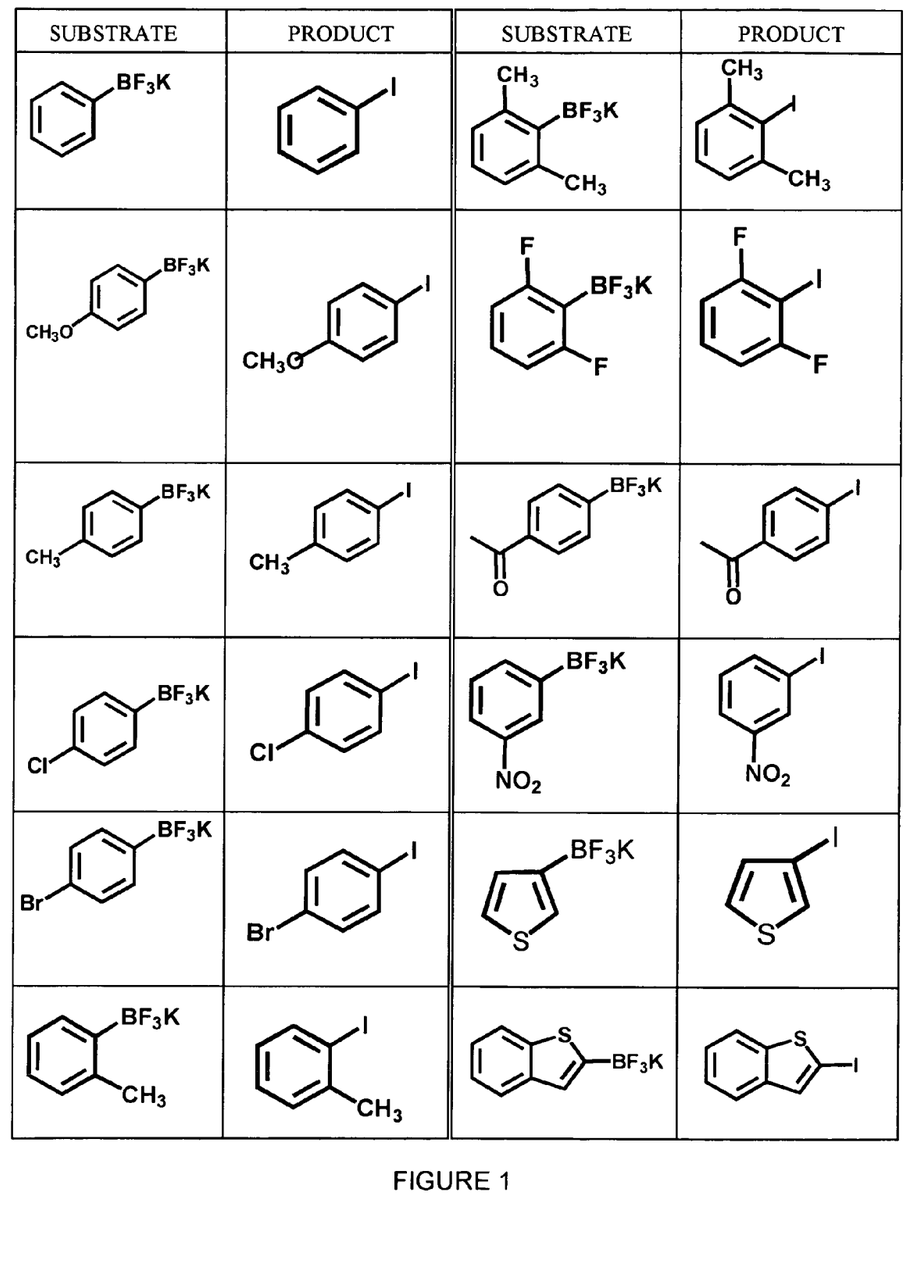
FIG. 1 shows representative aryltrifluoroborates and resultant aryliodides obtained by the method of the invention.

Representative aryliodides obtained are shown in FIG. 1. Table 1 shows the synthesis by the reaction of Scheme 3 of no-carrier added iodine-123 labeled iodoarenes from the corresponding aryltrifluoroborates.

TABLE 1

| ArBF$_3$K | Time of Reaction | Yield (%) |
|---|---|---|
| Phenyl | 15 minutes | 75 |
| 2,4,-Dimethylphenyl | 10 minutes | 79 |
| 4-Methoxyphenyl | 10 minutes | 88 |
| 4-Chlorophenyl | 3 hours | 51 |
| 4-Acetylphenyl | 5 hours | 29 |
| 3-Nitrophenyl | 12 hours | 0 |
| 1-Naphthalenyl | 15 minutes | 56 |
| 3-Thienyl | 30 minutes | 70 |

As shown in Table 1, the reaction of the invention resulted in the production of a variety of arylradioiodides. The radiochemical purity of the products was very high, typically greater than 98%, and the radiochemical yield generally exceeded 75%. The presence of a nitro group appeared to inhibit the reaction. It is noted that thienyltrifluoroborate, a heterocyclic analogue, underwent radioiodination smoothly and in good yield.

EXAMPLE 3

Synthesis of Vinyl (Alkenyl) Iodides

A variety of alkenyltrifluoroborates, as synthesized as described in Example 1, were subjected to radioiodination using no-carrier added Na$^{123}$I and peracetic acid in 50% aqueous THF to yield the corresponding alkenyliodides. The alkenylradioiodides were procedures using a method parallel to that in Example 2 for producing arylradioiodides. The general formula for this reaction is shown below in Scheme 4.

Scheme 4

$$RBF_3K \xrightarrow[\text{Chloramine-T}]{NaI} RI$$

R = Vinyl (alkenyl)

Figure 2:
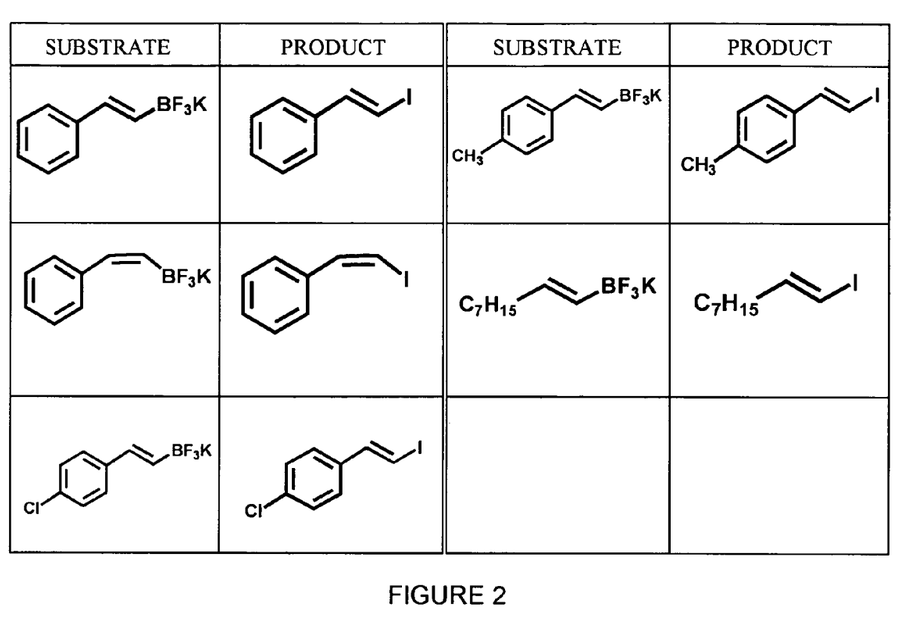
FIG. 2 shows representative vinyltrifluoroborates and resultant vinyliodides obtained by the method of the invention.

Representative alkenyliodides obtained are shown in FIG. 2. Table 2 shows the synthesis by the reaction of Scheme 4 of no-carrier added iodine-123 labeled vinyliodides from the corresponding vinyltrifluoroborates.

TABLE 2

| Vinyl-BF$_3$K | Yield (%) |
|---|---|
| Phenyl (trans) | 83 |
| Phenyl (cis) | 78 |
| 4-Methylphenyl | 90 |
| 4-Chlorophenyl | 86 |
| Heptyl | 58 |

As shown in Table 2, the reaction of the invention resulted in the production of a variety of vinylradioiodides. The radiochemical purity of the products was very high, typically greater than 98%, and the radiochemical yield generally exceeded 75%.

EXAMPLE 4

Synthesis of Alkynyl Iodides

A variety of alkynyltrifluoroborates, as synthesized as described in Example 1, were subjected to radioiodination using no-carrier added Na[123]I and peracetic acid in 50% aqueous THF to yield the corresponding alkenyliodides. The general formula for this reaction is shown below in Scheme 5.

Scheme 5

R = Alkynyl

Potassium alkynyltrifluoroborate precursors were prepared from the corresponding alkynes. Deprotonation of the corresponding terminal alkyne with n-BuLi at −78° C. in THF was followed by reaction of the lithium salt with trimethylborate. The transmetallation was performed at −78° C. for 1 hour and then at −20° C. for an additional hour. The resulting organoborate complex was allowed to react with $KHF_2$ at −20° C. for 1 hour and then at ambient temperature for 1 h to yield the desired potassium alkynyltrifluoroborate. All reactions were carried out using dry solvents under an inert atmosphere.

A variety of iodine-123 labeled alkynyl iodides were prepared from the corresponding alkynyltrifluoroborates. The results of this study are summarized in Table 3. Alkynyltrifluoroborates were subjected to radioiodination using no-carrier-added Na[123]I and peracetic acid in 50% aqueous THF to yield the corresponding alkynyliodide. The radiochemical purity of the products was typically >98% and the overall radiochemical yields generally exceed 85%.

EXAMPLE 4a

Synthesis of potassium (2-phenylethynyl)trifluoroborate (Representative Procedure for Preparing Potassium alkynyltrifluoroborates)

A solution of phenylacetylene (1.02 g, 10.0 mmol) in 20 mL of dry THF was cooled to −78° C. under argon. n-Butyllithium (6.25 mL, 1.60 M in hexane, 10 mmol) was added dropwise and the solution stirred for one hour. Trimethylborate (1.58 g, 15.0 mmol, 1.5 equiv) was then added dropwise at −78° C. and the solution stirred for one hour. The reaction mixture was then allowed to warm to −20° C. and stirred for an additional hour. A saturated aqueous solution of potassium hydrogen difluoride (4.70 g, 60.0 mmol, 6 equivalents) was added to the vigorously stirred solution. The resulting mixture was allowed to stir for one hour at −20° C., after which it was allowed to warm to room temperature. The solvent was removed under reduced pressure and the resulting white solid was dried under high vacuum for two hours to remove all water. The solid was then washed with acetone (20 mL) and then with hot acetone (20 mL). The resulting organic solution was filtered and the solvent removed to afford a white solid. The solid was recrystallized from hot acetonitrile to produce the desired product (1.41 g, 68%) whose physical and spectral properties were identical to those reported in the literature.

EXAMPLE 4b

Radiosynthesis of 1-[1[123]I]iodo-1-phenylethyne (Representative Procedure)

Alkynyltrifluoroborate (100 μL of $5.2 \times 10^{-2}$ in 50% aqueous tetrahydrofuran) was placed in a 2 mL Wheaton vial containing no-carrier-added Na[123]I (37 MBq in 0.1% aqueous NaOH). To this was added peracetic acid (100 μL, 0.3% solution in methanol). The reaction vial was sealed, covered with aluminum foil, and the mixture stirred for 15 min at room temperature. A drop of 10% aqueous sodium thiosulfate was added to decompose the excess iodine and the radioiodinated product was isolated by passing it through a silica gel Sep-pak using petroleum ether as eluent. The radiochemical purity of the 1-[$^{123}$I]iodo-2-phenylethyne was determined by radio-TLC (aluminum backed silica gel plate, hexane); $R_f$=0.68. The decay corrected radiochemical yield was determined to be 92% and radiochemical purity was 98%. The total synthesis time was 20 min.

Figure 3:
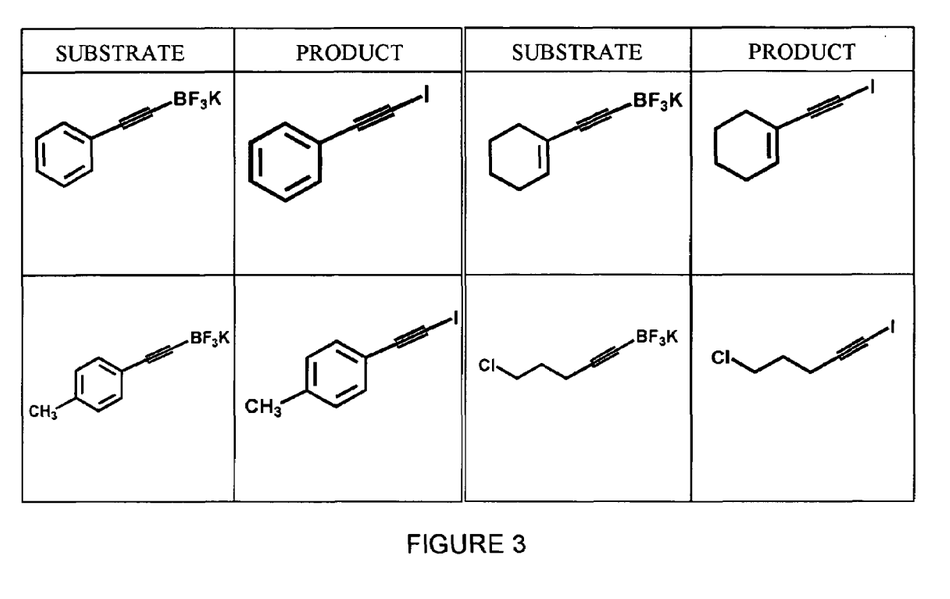
FIG. 3 shows representative alkynyltrifluoroborates and resultant alkynyliodides obtained by the method of the invention.

Representative alkynyliodides obtained are shown in FIG. 3. Table 3 shows the synthesis by the reaction of Scheme 5 of no-carrier added iodine-123 labeled alkynyliodides from the corresponding alkynyltrifluoroborates.

TABLE 3

| Alkynyl-BF$_3$K | Yield (%) |
|---|---|
| Phenyl | 92 |
| 4-Methoxyphenyl | 94 |
| 1-Cyclohexenyl | 90 |
| 1-Chlorophenyl | 91 |
| Hexyl | 88 |
| tert-Butyl | 85 |

As shown in Table 3, the reaction of the invention resulted in the production of a variety of alkynylradioiodides. The radiochemical purity of the products was very high, typically greater than 98%, and the radiochemical yield generally exceeded 85%.

EXAMPLE 5

Synthesis of Organic Bromides

A variety of bromine-76 labeled aryl, alkenyl, and alkynyl bromides were prepared from the corresponding aryl-, alkenyl-, and alkynyltrifluoroborate salts that were obtained as described in Example 1 as shown in Scheme 6. All the reactions were carried out using dry solvents under an inert atmosphere.

Scheme 6

R = Alkyl, alkenyl, alkynyl, aryl, or heteroaryl

Organotrifluoroborates were subjected to a radiobromination procedure using no-carrier added $NH_4{}^{76}Br$ and peracetic acid in 50% aqueous THF to yield the corresponding organobromides. Bromination of alkenyl trifluoroborates was found to proceed with retention of configuration, providing ready access to a variety of (E) and (Z) alkenyl bromides. The radiochemical purity of the products typically exceeds 98% and the overall radiochemical yields are good.

The radiobromination of alkynyltrifluoroborates produced radiochemical purities in excess of 98% and overall radiochemical yields of and 65%.

EXAMPLE 5a

Synthesis of potassium (2-phenylethynyl)trifluoroborate (Representative Procedure for Preparing Potassium alkynyltrifluoroborates)

A solution of phenylacetylene (1.02 g, 10.0 mmol) in 20 mL of dry THF was cooled to −78° C. under argon. n-Butyllithium (6.25 mL, 1.6 Min hexane, 10.0 mmol) was added dropwise and the solution was stirred for one hour at −78° C. Trimethylborate (1.58 g, 15.0 mmol) was then added dropwise at −78° C. and the solution was stirred for one hour. The reaction mixture was allowed to warm to −20° C. and stirred for an additional hour. A saturated aqueous solution of potassium hydrogen difluoride (4.7 g, 60.0 mmol) was added to the vigorously stirred solution. The resulting mixture was allowed to stir for one hour at −20° C., after which it was allowed to warm to room temperature. The solvent was removed under reduced pressure and the resulting white solid was dried under high vacuum for two hours to remove all water. The solid was then washed with acetone (20 mL), and then with hot acetone (20 mL). The resulting organic solution was filtered and the solvent removed to afford a white solid. The solid was recrystallized from hot acetonitrile to produce the desired product (1.41 g, 68%) whose physical and spectral properties were identical to those reported in the literature.

EXAMPLE 5b

Radiosynthesis of 1-[$^{76}$Br]bromo-2-phenylethyne (Representative Procedure)

No-carrier-added $NH_4$$^{76}$Br (3.7 MBq in 0.1% aqueous $NH_4OH$) was placed into a 2 mL Wheaton vial containing trifluoroborate (100 μL of 5.2×10$^{-2}$ M solution in 50% aqueous tetrahydrofuran). To this was added peracetic acid (100 μl, 0.3% solution in methanol). The reaction vial was sealed, covered with aluminum foil, and the mixture stirred for 10 min at room temperature. The radiobrominated product was isolated by passing through a silica gel Sep-Pak cartridge using petroleum ether as eluent. The radiochemical purity of the 1-[$^{76}$Br]bromo-2-phenylethyne was determined by radio-TLC (aluminum backed silica gel plate, hexane) $R_f$=0.73. The radiochemical (decay corrected) was found to be 80% and the radiochemical purity was >98%. The total synthesis time was 20 min. Alkenyltrifluoroborates were radiobrominated using the same procedure.

Figure 4:
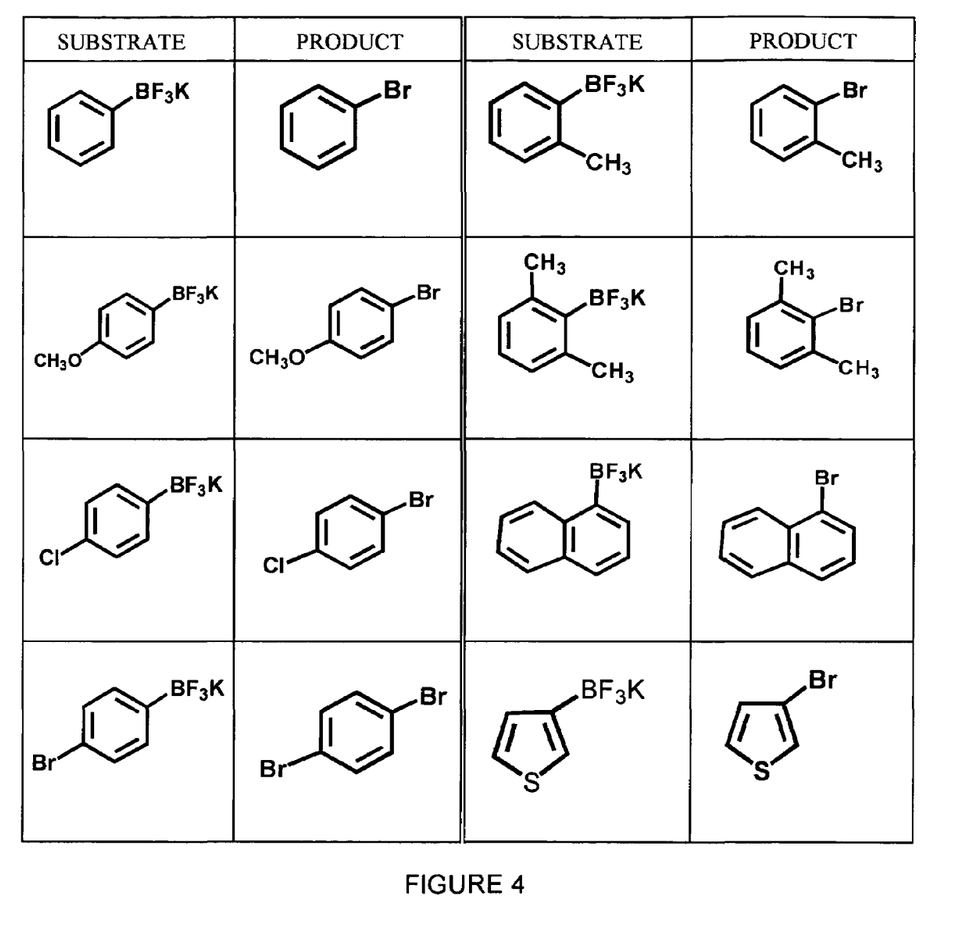
FIG. 4 shows representative aryltrifluoroborates and resultant arylbromides obtained by the method of the invention.
Figure 5:
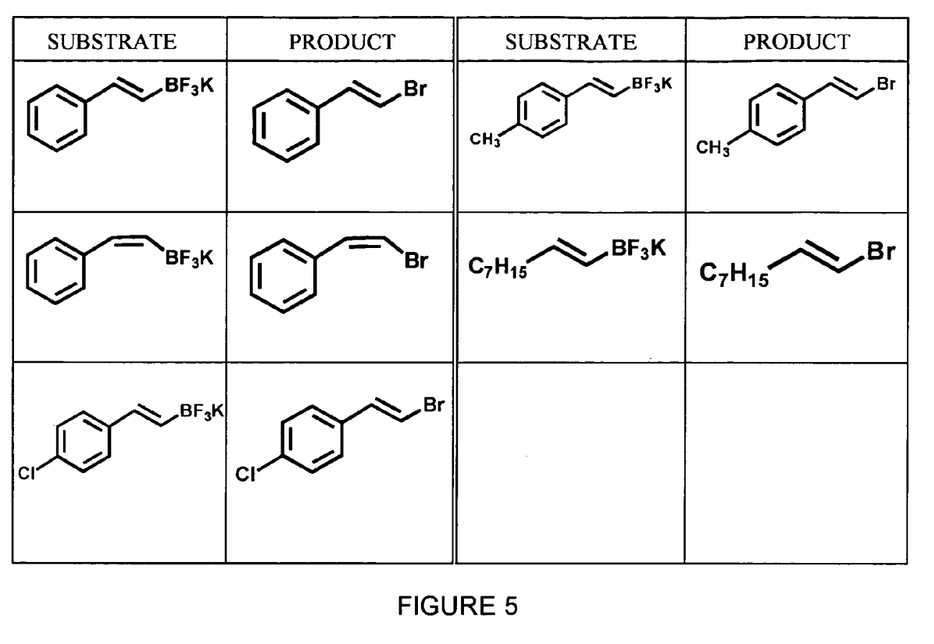
FIG. 5 shows representative vinyltrifluoroborates and resultant vinylbromides obtained by the method of the invention.
Figure 6:
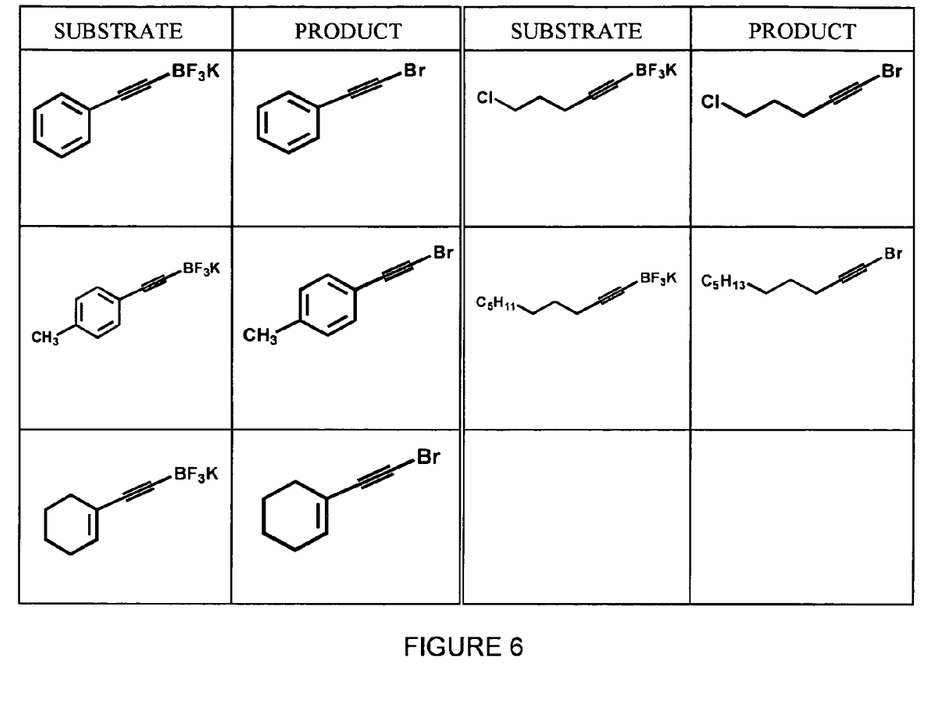
FIG. 6 shows representative alkynyltrifluoroborates and resultant alkynylbromides obtained by the method of the invention.

Representative organobromides obtained are shown in FIGS. 4, 5, and 6. Table 4 shows the synthesis by the reaction of Scheme 6 of no-carrier added bromine-76 labeled alkenylbromides from the corresponding alkenyltrifluoroborates.

TABLE 4

| Alkenyl-BF$_3$K | Yield (%) |
|---|---|
| Phenyl (trans) | 70 |
| Phenyl (cis) | 69 |
| 4-Methylphenyl | 74 |
| 4-Chlorophenyl | 65 |

TABLE 4-continued

| Alkenyl-BF$_3$K | Yield (%) |
|---|---|
| 4-Trifluoromethylphenyl | 56 |
| Heptyl | 48 |

As shown in Table 4 the reaction of the invention resulted in the production of a variety of alkenylradiobromides. The radiochemical purity of the products was very high, typically greater than 98%, and the radiochemical yield generally exceeded 60%.

Table 5 shows the synthesis by the reaction of Scheme 6 of no-carrier added bromine-76 labeled alkynylbromides from the corresponding alkynyltrifluoroborates.

TABLE 5

| Alkynyl-BF$_3$K | Yield (%) |
|---|---|
| Phenyl | 80 |
| 4-Methoxyphenyl | 82 |
| 4-Methylphenyl | 84 |
| 4-Cyanophenyl | 78 |
| 1-Cyclohexenyl | 64 |
| Hexyl | 81 |
| t-Butyl | 68 |
| 1-Chloropropyl | 76 |
| Tert-Butyldimethylsilyloxybutyl | 78 |
| 1-Hydroxybutyl | 65 |

As shown in Table 5 the reaction of the invention resulted in the production of a variety of alkynylradiobromides. The radiochemical purity of the products was very high, typically greater than 98%, and the radiochemical yield generally exceeded 70%.

EXAMPLE 6

Synthesis of Radioiodinated Rofecoxib

Figure 7:
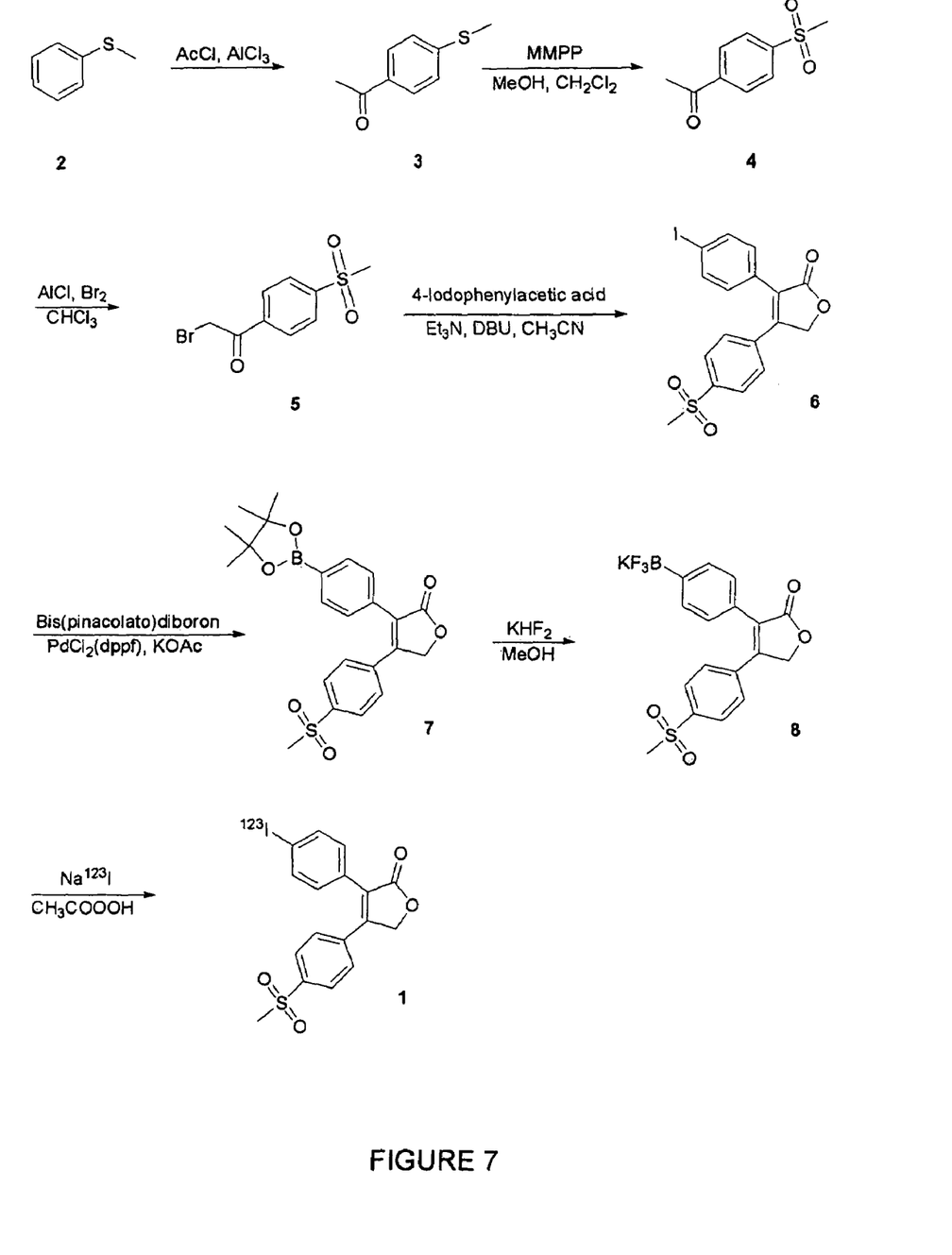
FIG. 7 shows a scheme for the synthesis of radioiodinated rofecoxib.

FIG. 7 outlines the synthesis of a no-carrier-added iodine-123 labeled analogue of rofecoxib 1. Thioanisole 2 was converted to the requisite potassium trifluoroboronate salt 8 in six steps. Ketone 3 was prepared by Friedel-Crafts acylation of thioanisole 2. Oxidation of 3 using MMPP (magnesium monoperoxyphthalate hexahydrate) afforded sulfone 4 which was allowed to react with bromine in chloroform at 0° C. in the presence of a trace amount of $AlCl_3$ to generate 5. Bromoketone 5 was then coupled with 4-iodophenylacetic acid and then cyclized in the presence of triethylamine and DBU to produce 6 (the non radioactive analogue of the target molecule 1) in 52% yield. Compound 6 was converted to boronic ester 7 using Suzuki chemistry. Addition of $KHF_2$ then generated the trifluoroborate 8. Compound 8 was then reacted according to the method of the invention to generate the no-carrier-added radioiodinated 1. The radiochemical purity of the product exceeded 98% as revealed by radio TLC and the radiochemical yield was 42%.

This scheme shows clearly how the method of the invention can be used to place a halogenation site at a desired location on a complex molecule, such as rofecoxib, by attaching a binding site for a halogen or a radiolabel on an intermediate in the synthesis of a final molecule and later attaching the halogen or the radiolabel at the site following synthesis of the trifluoroboronated final molecule.

Further modifications, uses, and applications of the invention described herein will be apparent to those skilled in the art. It is intended that such modifications be encompassed in the claims that follow.

The invention claimed is:

1. A method for halogenating an organic chemical compound comprising obtaining an organic compound in the form of an organotrifluoroborate and reacting the organotrifluoroborate with a halide ion in the presence of an oxidizing agent, thereby obtaining a halogenated organic compound.

2. The method of claim 1 wherein the organotrifluoroborate and the halide ion are in solution when reacted.

3. The method of claim 1 wherein the organotrifluoroborate is a potassium organotrifluoroborate.

4. The method of claim 1 wherein the organotrifluoroborate includes an organic moiety selected from the group consisting of aryl, heteroaryl, alkenyl, vinyl, alkynyl, and alkyl.

5. The method of claim 1 wherein the halide ion is an ion of fluorine, iodine, bromine, or astatine.

6. The method of claim 1 wherein the halide ion is radioactive.

7. The method of claim 1 wherein the oxidizing agent is selected from the group consisting of air, a peracid, a peroxide, chloramine-T, halosuccinimide, tert-butylhydroperoxide, meta-chlorperoxybenzoic acid (m-CPBA), and a halogen.

8. The method of claim 1 wherein the reaction is performed in the presence of a catalytic quantity of an acid or base.

9. A method for radiohalogenating an organic chemical compound comprising obtaining an organic compound in the form of an organotrifluoroborate and reacting the organotrifluoroborate with a radioactive halide ion in the presence of an oxidizing agent, thereby obtaining a radiohalogenated organic compound.

10. The method of claim 9 wherein the organotrifluoroborate and the radioactive halide ion are in solution when reacted.

11. The method of claim 9 wherein the organotrifluoroborate is a potassium organotrifluoroborate.

12. The method of claim 9 wherein the organotrifluoroborate includes an organic moiety selected from the group consisting of aryl, heteroaryl, alkenyl, vinyl, alkynyl, and alkyl.

13. The method of claim 9 wherein the radioactive halide ion is an ion of fluorine, iodine, bromine, or astatine.

14. The method of claim 13 wherein the radioactive halide ion is selected from the group consisting of fluorine-18, bromine-82, iodine-123, and astatine-211.

15. The method of claim 9 wherein the oxidizing agent is selected from the group consisting of air, a peracid, a peroxide, chloramine-T, halosuccinimide, tert-butylhydroperoxide, meta-chlorperoxybenzoic acid (m-CPBA), and a halogen.

16. The method of claim 9 wherein the reaction is performed in the presence of a catalytic quantity of an acid or base.

* * * * *